(12) United States Patent
Farmer

(10) Patent No.: US 11,344,675 B2
(45) Date of Patent: May 31, 2022

(54) INJECTION DEVICE WITH DELIVER PHASE VELOCITY REGULATOR

(71) Applicant: OWEN MUMFORD LTD., Oxfordshire (GB)

(72) Inventor: Matthew David Farmer, Oxfordshire (GB)

(73) Assignee: Owen Mumford Limited, Oxfordshire (GB)

(*) Notice: Subject to any disclaimer, the term of this patent is extended or adjusted under 35 U.S.C. 154(b) by 241 days.

(21) Appl. No.: 16/494,513

(22) PCT Filed: Mar. 15, 2018

(86) PCT No.: PCT/GB2018/050662
§ 371 (c)(1),
(2) Date: Sep. 16, 2019

(87) PCT Pub. No.: WO2018/167492
PCT Pub. Date: Sep. 20, 2018

(65) Prior Publication Data
US 2020/0086050 A1    Mar. 19, 2020

(30) Foreign Application Priority Data
Mar. 15, 2017 (GB) ..................... 1704137

(51) Int. Cl.
*A61M 5/20* (2006.01)
*A61M 5/24* (2006.01)
(Continued)

(52) U.S. Cl.
CPC ............ *A61M 5/2033* (2013.01); *A61M 5/24* (2013.01); *A61M 5/28* (2013.01);
(Continued)

(58) Field of Classification Search
CPC ........ A61M 5/2033; A61M 5/24; A61M 5/28; A61M 5/31511; A61M 2005/206; A61M 2005/208
See application file for complete search history.

(56) References Cited

U.S. PATENT DOCUMENTS

2016/0193416 A1    7/2016 Olson

FOREIGN PATENT DOCUMENTS

AU    1325995 A    7/1995
EP    1790366 A1    5/2007
(Continued)

OTHER PUBLICATIONS

First Office Action from corresponding Chinese Patent Application No. 201880032468.5 dated Mar. 29, 2021 (15 pages) (English translation included).
(Continued)

*Primary Examiner* — Bhisma Mehta
*Assistant Examiner* — Neeraja Gollamudi
(74) *Attorney, Agent, or Firm* — Quarles & Brady LLP

(57) ABSTRACT

Disclosed is an injection device for delivering a medicament from a syringe contained within a housing, the device being configured to move the syringe through the housing to cause insertion of a needle of the syringe into a user's skin and move a syringe bung through a syringe body, delivering medicament through the needle. The device includes: a plunger engaging the bung; a sleeve around the plunger; an insertion spring biasing the sleeve to the housing; and a delivery spring biasing the plunger to the sleeve. A release mechanism releases the sleeve from the housing to commence insertion and release the plunger from the sleeve, following insertion, delivering medicament. A velocity regulator regulates the plunger upon release and disengages during delivery, and includes a screw thread associated with the sleeve or plunger and one or more thread engaging members formed on the other of the sleeve and the plunger.

16 Claims, 8 Drawing Sheets

(51) Int. Cl.
*A61M 5/28* (2006.01)
*A61M 5/315* (2006.01)
*A61M 5/31* (2006.01)

(52) U.S. Cl.
CPC ... *A61M 5/31511* (2013.01); *A61M 2005/206* (2013.01); *A61M 2005/208* (2013.01); *A61M 2005/3143* (2013.01)

(56) References Cited

FOREIGN PATENT DOCUMENTS

| | | | | |
|---|---|---|---|---|
| GB | 2 538 566 | 11/2016 | | |
| WO | 9516481 A1 | 6/1995 | | |
| WO | WO 2011/101381 | 8/2011 | | |
| WO | WO-2011101381 A2 * | 8/2011 | .......... | A61M 5/1452 |
| WO | WO 2011/162686 | 12/2011 | | |
| WO | WO 2012/049484 | 4/2012 | | |
| WO | WO 2014/060563 | 4/2014 | | |
| WO | WO 2015/011488 | 1/2015 | | |
| WO | WO 2016/189286 | 12/2016 | | |
| WO | WO 2017/007850 | 1/2017 | | |
| WO | WO-2017007850 A1 * | 1/2017 | .......... | A61M 5/3287 |

OTHER PUBLICATIONS

International Search Report, PCT/GB2018/050662, dated Jul. 3, 2018.
Great Britain Search Report, GB1704137.7, dated Aug. 11, 2017.
Written Opinion, PCT/GB2018/050662, dated Jul. 3, 2018.

* cited by examiner

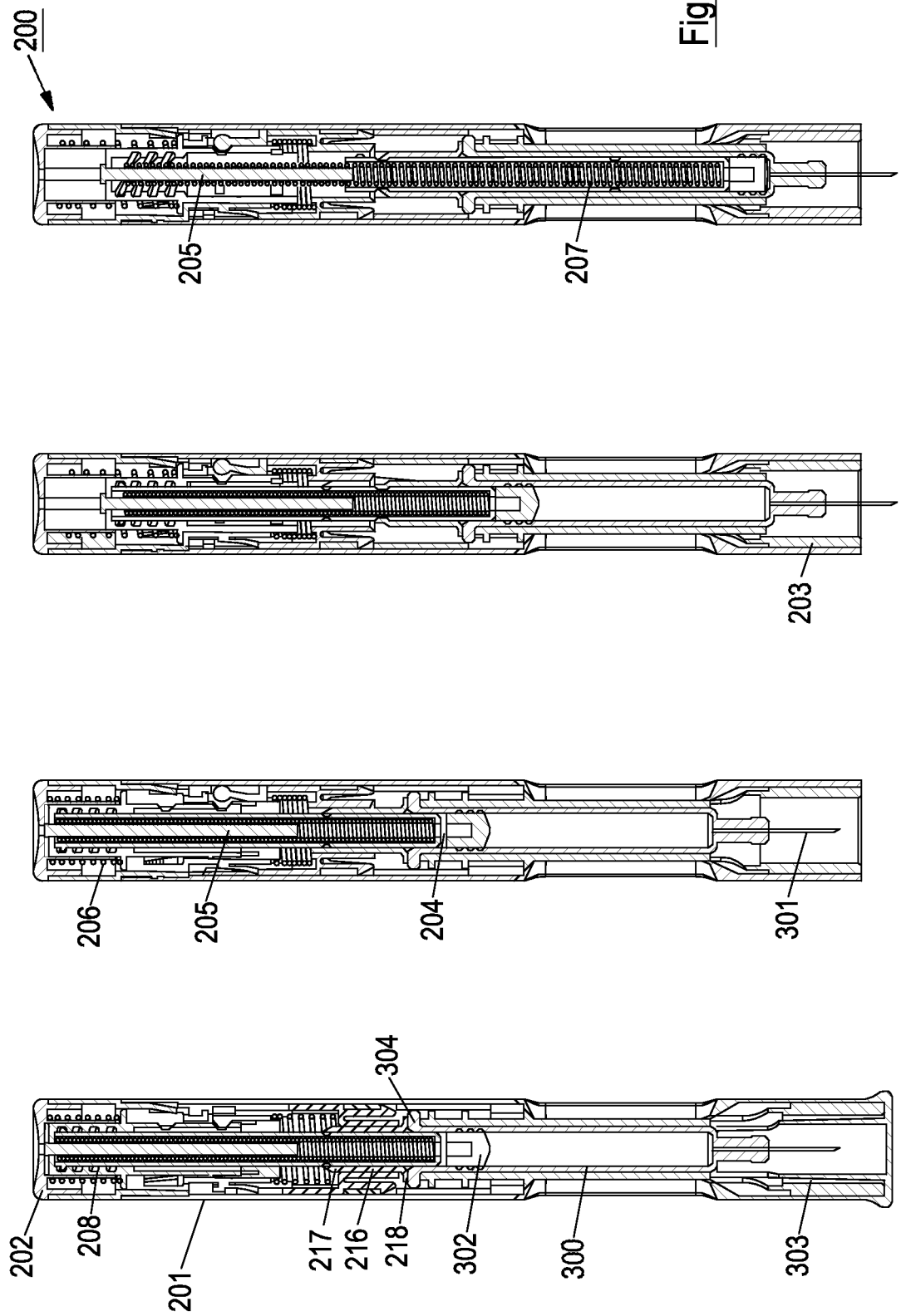

INJECTION DEVICE WITH DELIVER PHASE VELOCITY REGULATOR

CROSS-REFERENCE TO RELATED APPLICATIONS

The present application represents the United States National Stage of International Application No. PCT/GB2018/050662, filed Mar. 15, 2018, which claims priority to British Patent Application Serial No. GB 1704137.7, filed Mar. 15, 2017, and entitled, "INJECTION DEVICE WITH DELIVER PHASE VELOCITY REGULATOR," the contents of which are incorporated herein by reference in their entirety.

TECHNICAL FIELD

This invention relates to injection devices for delivering a dose of medicament from a syringe. In particular, though not necessarily, the invention relates to an autoinjector type device which facilitates powered or power assisted needle insertion and drug delivery.

BACKGROUND

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament such as Insulin. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an "autoinjector" device, in which, in addition to automating the delivery of the medicament, the device is also arranged to automate the insertion of a needle into the skin prior to the delivery of the medicament.

Injection devices generally comprise a delivery arrangement which is arranged to automatically deliver a dose from the syringe, and optionally (in the case of an autoinjector) to first displace the syringe within the housing to cause needle penetration. The delivery arrangement generally acts via a plunger which includes or engages a piston (also referred to as a "bung") which is slidably provided within the syringe. In the case of an autoinjector the initial static friction or "stiction" between the bung and syringe resists forward movement of the piston relative to the syringe such that initially the delivery arrangement moves the syringe and piston forward into the needle insertion position. Here, further movement of the syringe is blocked and the delivery arrangement will continue to move forward, overcoming the stiction, and moving the piston and the bung through the syringe.

A common form of delivery arrangement includes an actuation mechanism which biases the plunger forwardly and a trigger mechanism which holds the plunger (directly or indirectly) against the force of the actuation mechanism until the trigger is released. For example the actuation mechanism may comprise a drive spring (for example a compression spring) which is held in an energised (or primed position) prior to release by the trigger.

An injection device of the autoinjector type is described in WO2016/189286. The actuation mechanism of this device comprises two springs, a first, relatively weak, insertion spring for moving the syringe through the device housing to insert the needle into the skin and a second, relatively strong, delivery spring for driving the plunger and piston through the syringe body.

WO2016/189286 addresses a known problem with autoinjectors, namely that the force exerted by the insertion spring during the needle insertion phase may be great enough to damage the syringe when it bottoms out against the housing at the end of its travel. The problem is mitigated by incorporating a velocity regulator which limits the velocity of the syringe until it has bottomed out.

SUMMARY

According to the present invention there is provided an injection device for delivering a medicament from a syringe contained, in use, within a housing of the device, the device being configured to move the syringe through the housing to cause insertion of a needle of the syringe into a user's skin and to subsequently move a bung of the syringe through a syringe body to deliver medicament through the needle. The device comprises a plunger for engaging with said bung, a sleeve located around the plunger, an insertion spring biasing the sleeve relative to the housing, and a delivery spring biasing the plunger relative to the sleeve. The device further comprises a release mechanism for releasing the sleeve from the housing to commence insertion and for releasing the plunger from the sleeve, following insertion, to commence delivery of the medicament, and a velocity regulator for regulating the velocity of the plunger upon its release from the sleeve and for disengaging from the plunger during delivery, the velocity regulator comprising a screw thread associated with one of the sleeve and the plunger and one or more thread engaging members formed on the other of the sleeve and the plunger.

BRIEF DESCRIPTION OF THE DRAWINGS

FIG. 7 is a cross-sectional view of an injection device in a pre-fired state.

DETAILED DESCRIPTION

In the following embodiments, the terms "forward" and "front" refer to the patient facing end of the injection device or component thereof. In other words, the front end of the injection device is the end proximal to the injection site during use. Likewise, the term "rear" refers to the nonpatient end of the injection device assembly or component thereof. In other words, the term "rear" means distant or remote from the injection site during use.

Axial, radial and circumferential are used herein to conveniently refer to the general directions relative to the longitudinal direction of the injection device (or components thereof). The skilled person will, however, appreciated that these terms are not intended to be narrowly interpreted (and for example the injection device may have a non-circular and/or irregular form). Typically, regardless of the chosen injection device external profile the syringe or cartridge will have a conventional, generally cylindrical, elongate form and will include or be associated with a needle extending longitudinally from a forward end thereof. Thus, the longitudinal axis of the injection device will typically substantially coincide with (or be parallel to) the axial direction of the syringe or cartridge.

Figure 1:
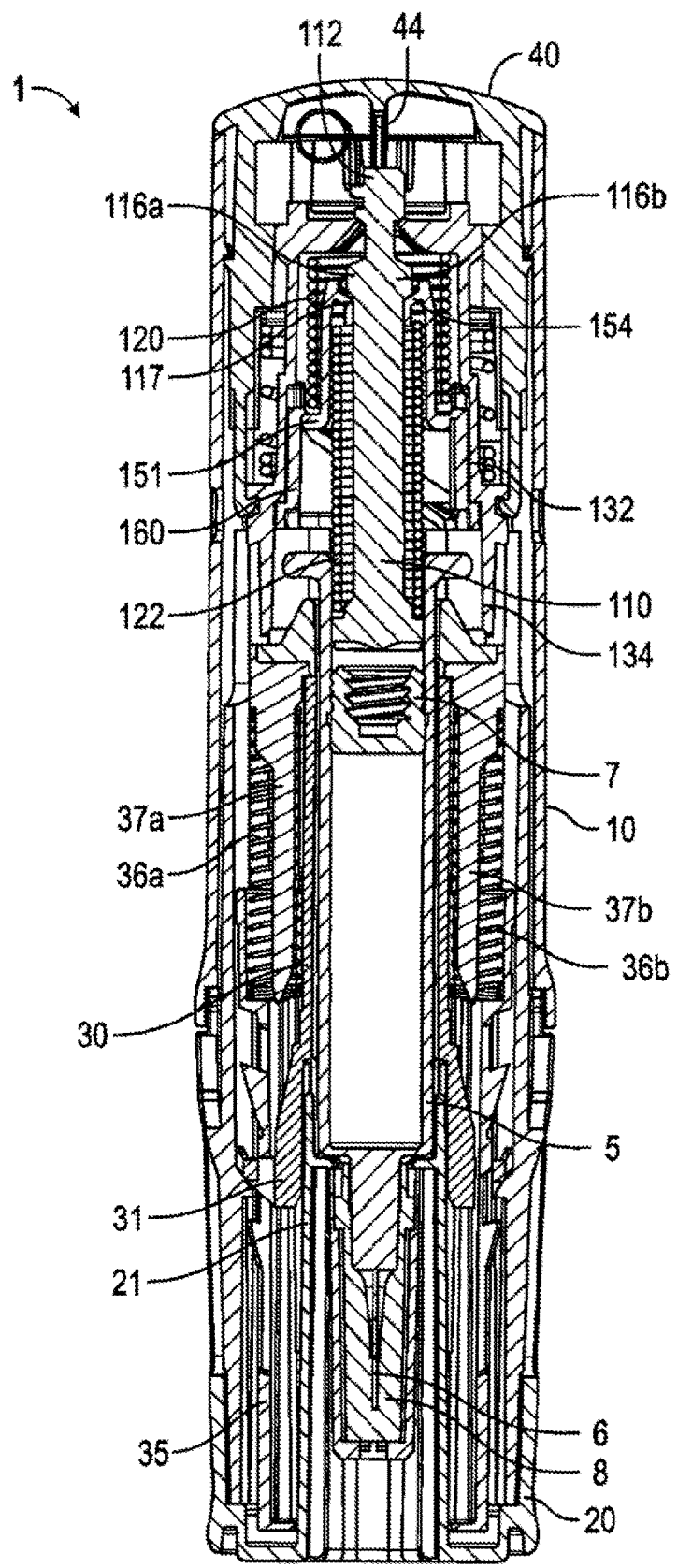
FIG. 1 is a cross-sectional view of a prior art autoinjector.

FIG. 1 shows a cross-sectional view of a prior art autoinjector 1 as disclosed in WO2016/189286. The autoinjector comprises a housing 10 within which is provided a syringe 5 of medicament. The housing 10 has a generally elongate tubular shape with a generally oval cross-sectional profile (and has a longitudinal axis running through the centre of the syringe).

The syringe 5 is a conventional syringe having a bung 7 within its body and a needle 6 at its forward end which may be initially protected (so as to remain sterile) by a removable needle shield or "boot" 8. The illustrated autoinjector 1 is generally intended to be a single use device and, therefore, the view of FIG. 1 may typically represent a fully assembled, ready to use device as provided to an end user. A cap 20 is provided which closes the forward end of the autoinjector 1 prior to use. The cap 20 includes an internal formation, comprising rearwardly extending members 21, arranged to engage the removable needle shield 8 of the syringe 5 such that removal of the cap 20 from the housing 10 during use also removes the removable needle shield 8 from the syringe 5.

The autoinjector 1 comprises a forward subassembly in a forward portion of the housing 10 and a rearward assembly in a rearward portion of the housing 10. The two housing portions may be snap fit together, about the syringe, during assembly. The forward subassembly comprises the components which surround and/or are initially forward of the syringe 5. The rearward subassembly comprises those components which are initially rearward of the syringe 5.

A forward portion of the housing 10 contains a syringe carrier 30 for movably mounting the syringe within the housing 10 to enable automatic needle penetration. It is noted that prior to the removal of the cap 20, the rearwardly extending members 21 of the cap 20 underlie spring fingers 31 of the syringe carrier 30. This arrangement thus prevents inward movement of the spring fingers 31 prior to removal of the cap 20 and, therefore, blocks unlatching of the syringe carrier 30 and prevents movement relative to the housing 20.

A needle shroud 35 is also provided and arranged to shroud the needle after use (when the syringe 5 and syringe carrier 30 are in a forward position) to prevent needle stick injuries. The shroud 35 is be activated by a pair of side-by-side shroud springs 36a, 36b carried on respective spring guides 37a, 37b. Operation of the shroud 30 and carrier 35 is not described here in any detail. However, it is noted that the arrangement substantially corresponds to the arrangement described in WO2012/085580.

A rearward portion of the housing 10 includes a trigger button 40 which is inserted into the rearward portion of the housing 10 from the rearward end so as to substantially close the rearward end of the housing 10. The trigger button 40 has a cup-like profile with side walls which are arranged to fit within (and be substantially concentric with) the rearward housing 30 and an end wall which closes the rear end of the housing. The trigger button 40 includes a pair of forwardly extending resilient arms 41a and 41b which are arranged to provide an engagement between the trigger button 40 and the injector 1.

Figure 2:
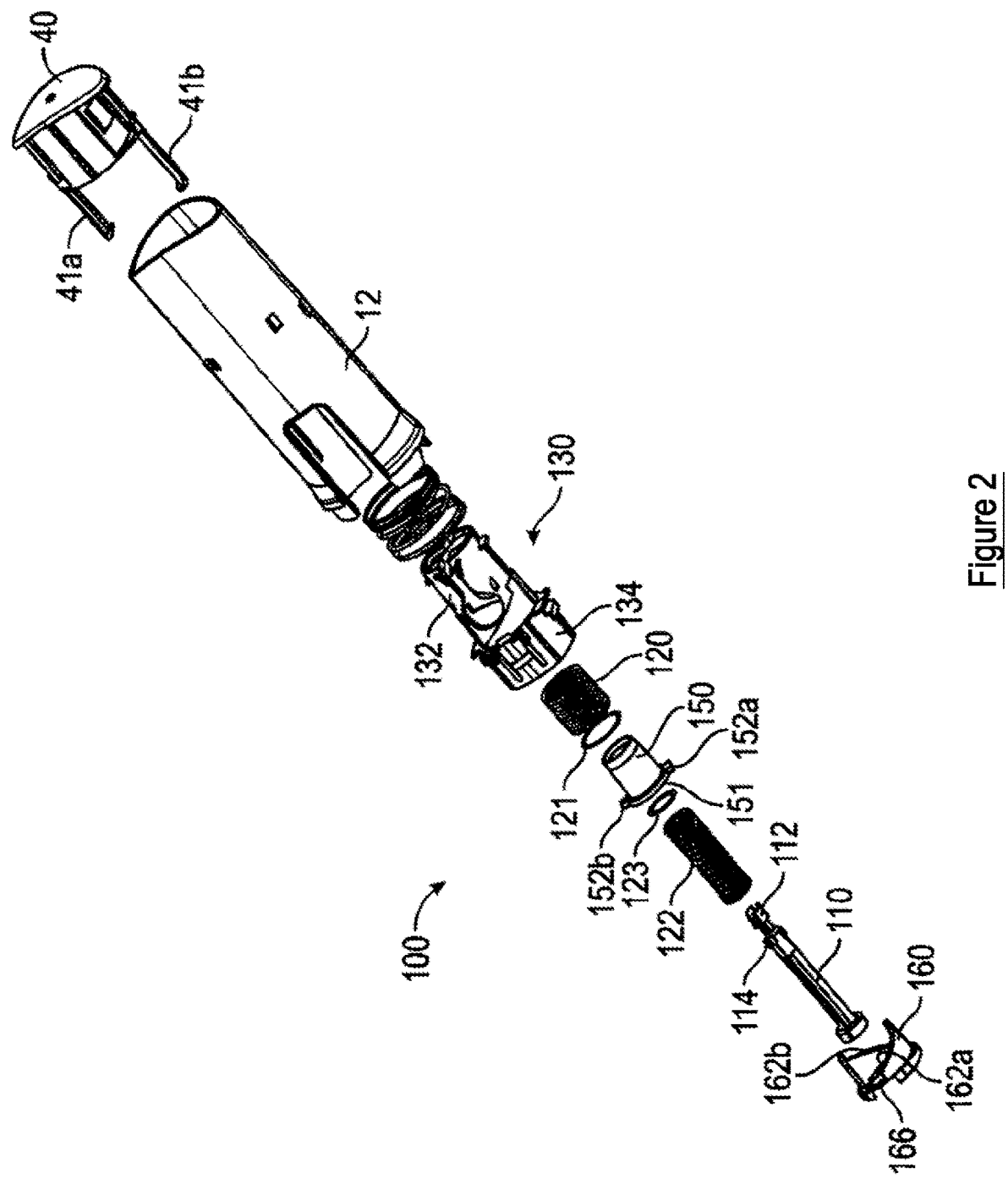
FIG. 2 is an exploded view of a rear section of the autoinjector of FIG. 1.

The rearward portion of the housing 10 also includes a drive mechanism 100, best seen in FIG. 2. The drive mechanism 100 includes a plunger 110 which is arranged to engage the bung 7 of the syringe 5 in use. The plunger 110 is driven forwards in use by a pair of concentric drive springs 120 and 122 (although it will be appreciated that in other embodiments a single spring may be used). An intermediate drive member in the form of a collar 150 (which also functions as part of the velocity regulator as described below) is provided between the first 120 and second 122 drive springs. A pair of thrust washers 121, 123 are provided respectively between the first 120 and second 122 springs and the drive member/collar 150. A latch 130 is arranged concentrically around the drive springs 120, 122, intermediate member/collar 150 and plunger 110. The latch 130 is arranged to hold the plunger 110 against the bias of the springs 120, 122 until the latch is released via the trigger button 40. The latch 130 comprises a rear body portion 132 having a split cylinder profile and defining a latch aperture at its rear end and a forward connecting body portion 134. The basic functional operation of the drive mechanism 100 is substantially as described, for example, in WO2012/049484 and WO2015/011488.

The actuation mechanism will now be described in further detail with particular reference to FIGS. 2 and 3 to 6.

FIG. 2 shows an exploded view of a rearward subassembly of the autoinjector device 1 (in which it may be noted that the housing 10 includes a discreet rearward housing component 12). In FIG. 3A the housing is omitted for clarity and in FIGS. 3B and 3C only the components directly associated with the velocity regulator are shown for further clarity. As noted above, the actuation mechanism includes a latch member 130 which is removably fixed into the housing 10 (by a snap fit arrangement) and initially retains the plunger 110 against the forward biasing force of the actuation springs 120 and 122 (which act via the intermediate member 150). At the rear of the injection device 1 is provided a trigger button 40 which is initially retained in position by the pair of arms 41a, 41b. In a central portion of the inner surface of the rearward face of the button 40, a forwardly extending boss 44 is provided which acts to urge the plunger 110 out of engagement with the latch member 130 during activation (in a manner such as that described in the applicants earlier patent applications referred to above).

The boss 44 comprises an arrangement which is in splined engagement with the rearward head 112 of the plunger 110. It will be seen that the rearward end of the plunger 110 is provided with a pair of axially extending radial slots which extend forwardly from the head 112 and the boss 44 comprising a corresponding pair of projections. As will be explained in further detail below, this arrangement ensures that the plunger 110 is rotationally fixed relative to the trigger button 40. In turn the trigger button 40 is non-rotationally engaged with the housing 10 (for example, due to the non-circular shape of the housing 10 and trigger button 40 and/or the engagement between the legs 41a, 41b of the trigger button 40 and the latch 130).

The actuation mechanism 100 of the autoinjector device 1 also includes a velocity regulator arranged to control or limit the initial velocity of the plunger 110 upon release of the actuation mechanism. The velocity regulator utilises a cam member 152 which travels along a cam surface 162 which provides an inclined plane along which the cam member 152 will travel during actuation.

The cam surface 162 is conveniently provided on a cam body 160 which is engaged with the forward portion 134 of the latch 130 by a snap-fit arrangement including, for example, at least one latch member 166. To ensure proper alignment between the cam body 160 and the latch member 130, an alignment flange 167 may also be provided on the cam body 160 to abut a corresponding shoulder 135 in the latch 130. The cam body 160 may comprise a generally annular body with an external profile which matches the required internal profile of the latch 130. A pair of helical cam surfaces 162a, 162b are defined at the rearward end of the cam body and are forwardly sloped to define a pair of parallel cam paths which extend circumferentially around the interior of the injection device 1 whilst also being inclined forwardly in the manner of a partial screw thread. A correspondingly profiled shoulder may be provided rearwardly of the cam surface 162 on the interior surface of the latch 130 such that when the cam body is assembled with the latch 130, a slot or track 138 is defined (and configured to receive the cam members 152). Each cam surface 162 is provided with stop 163 at its rearward end (which acts to separate the separate cam paths defined by the cam body 160) and ends with a cut-out or aperture 164 at the forwardmost end of the cam surface 162.

Figure 3:
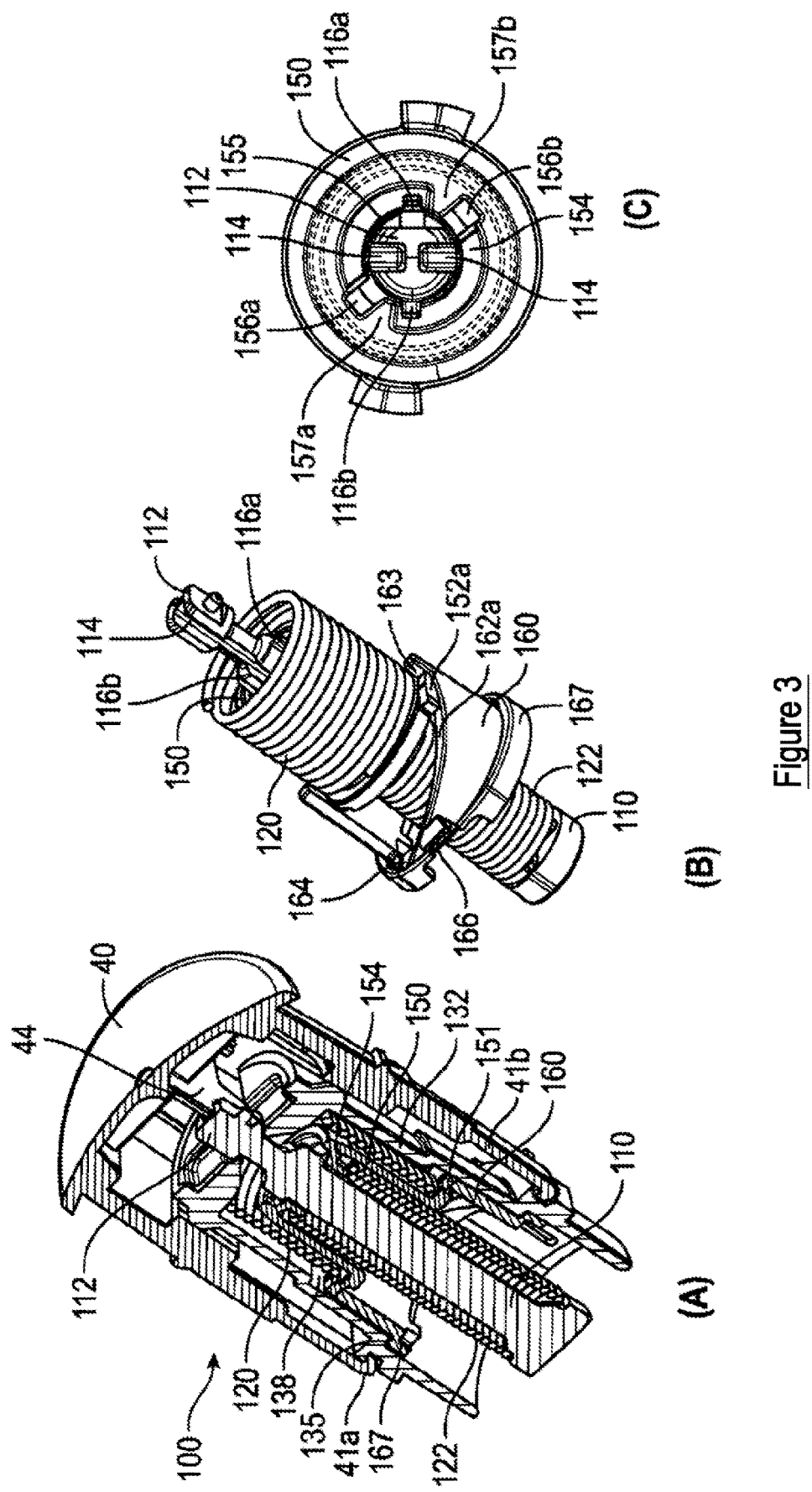
FIG. 3 is a cross-sectional view and partial end view of an actuation mechanism including a velocity regulator of the autoinjector of FIG. 1, in a pre-fired state.
Figure 4:
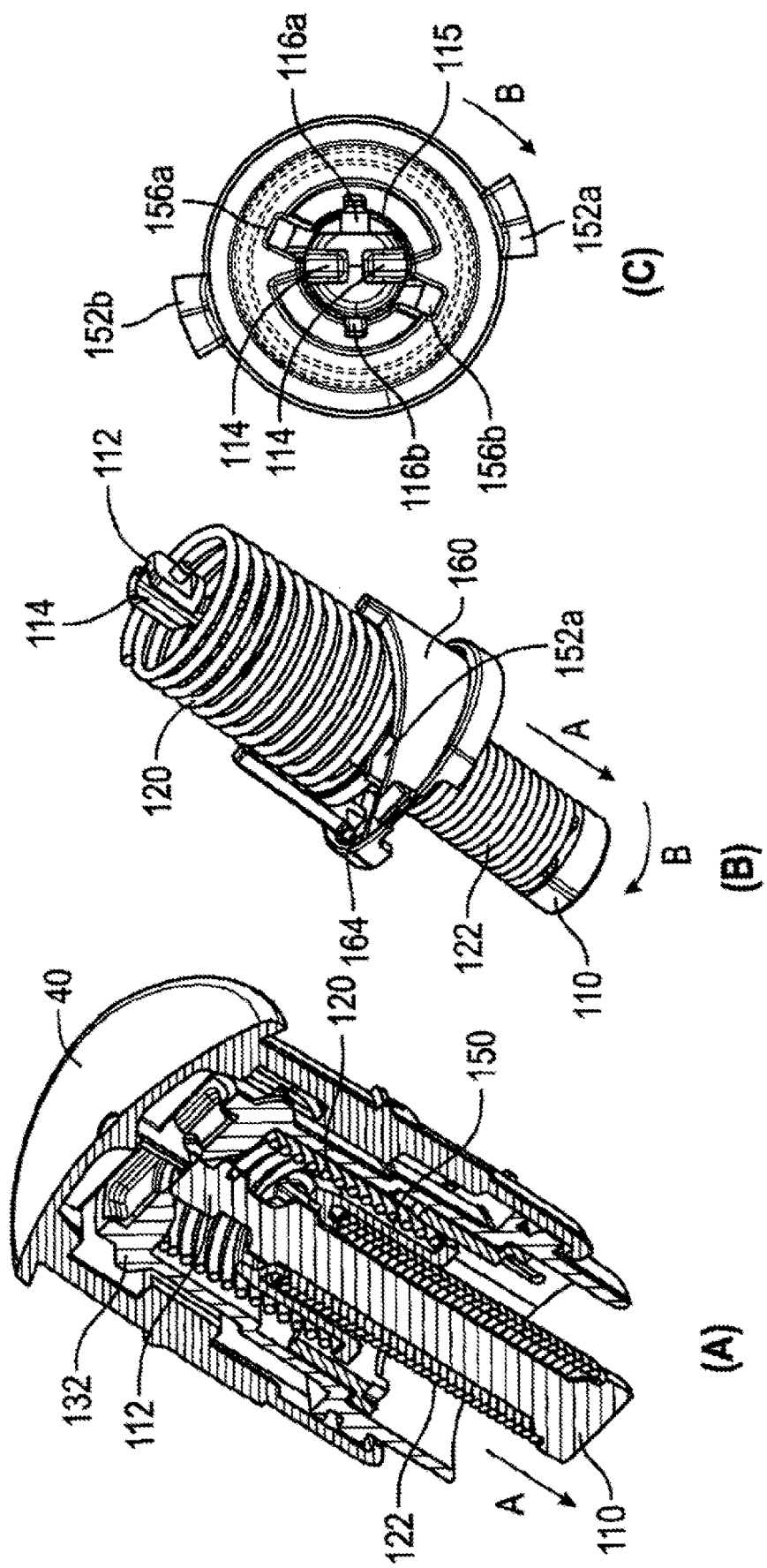
FIGS. 4 to 6 are sequential views corresponding to FIG. 3 during the activation of the autoinjector of FIG. 1.

The collar 150 acts as an intermediate drive member between the first compression spring 120 and second compression spring 122. Accordingly, the collar 150 includes an external radial flange 151 at its forward end which provides a seat for the first compression spring 120 and an internal radial flange 154 at its rearward end which provides a seat for the second compression spring 122. The thrust washers 121, 123 are disposed on the seats between the radial flanges 151, 154 of the collar and the springs 120, 122. The collar 150 is a generally cylindrical body and is provided with a pair of radially opposed outwardly extending lugs 152a, 152b. The lugs 152a, 152b are provided on a radially outer surface of the outwardly extending flange 151 (such that they do not impede either of the compression springs 120, 122). The internal flange 154 at the rear of the collar 150 includes an aperture 155 through which the head 112 of the plunger extends when the actuation mechanism 100 is in the pre-fired (or primed) condition as shown in FIG. 3.

The aperture 155 is provided with a keyed profile defined by a cylindrical central aperture portion 155a and a pair of opposed radial slots 156. The cylindrical side walls of the collar 150 extend rearwardly, slightly beyond the flange 154 so as to define a cylindrical cup which surrounds the flange 154 and the aperture 155. Inwardly radially extending stop members 157a, 157b may be provided adjacent to one side of the radial slots 156a and 156b.

A rearward portion of the plunger 110 which is axially rearward of the aperture 155 in the pre-fired configuration is provided with a profiled cross-section for engagement with the keyway defined by the aperture 155. This profiled portion is immediately forward of the head 112 of the plunger which is configured to be engaged by the latch 130. The profiled portion is defined by a pair of radially outwardly extending projections 116a, 116b which provide a forward facing shoulder 117 is initially engaged with the rearward face of the flange 154. The radial projections 116a, 116b are configured such that they may pass through the radial slots 156a, 156b when the slots 156 and projections 116 are aligned.

The actuation sequence of the mechanism 100 and velocity regulator will now be described with reference to FIGS. 3 to 6. The pre-firing configuration of the actuation mechanism 100 is shown in FIG. 3. In this configuration the head 112 of the plunger 110 is retained in the aperture of the latch 130. As such both the first compression spring 120 and the second compression spring 122 are in a compressed, energised, state. The trigger button 40 is in splined engagement with the rearward end of the plunger 110 via the boss 44 being positioned within the slots 114 at the rear of the plunger 110. The rearward portion 132 of the latch 130 is unable to expand to release the head 112 of the plunger 110 as part of the trigger button abuts an outer surface of the rearward section of the latch 132.

In this position the radial projection 116 of the plunger 110 is rearwardly positioned relative to the aperture 155 of the collar 150 and the relative rotational position of the plunger 110 and the collar 150 has been set during assembly such that the projections 116 are misaligned with the slots 116 and, in fact, it will be noted that the projections 156 abut against the stops 157 of the collar 150. In this initial position the cam members 152 are positioned at a rearward end of the cam surfaces 162 and essentially abut against the stops 163 at the rearwardmost end of the cam surfaces 162.

In order to activate the device the user urges the trigger button 40 forwardly relative to the housing 10 of the autoinjector device 1 (having firstly carried out any required initiation steps such as removal of the cap from the forward end of the autoinjector device 1 and/or releasing any safety mechanisms, such as an interlock). The forward movement of the trigger button 40 moves the blocking arrangement of the cap 40 out of alignment with the rearward section 132 of the latch 130 and may also directly transmit a forward force onto the rear of the plunger 110 via the engagement of the boss 44 with the head 112 of the plunger 110. As the result of this trigger action, the head 112 of the plunger 110 is released from the trigger 130 freeing the rearward spring 120 to urge the plunger forwardly, in the direction of arrow A, via the outer flange 151 or the collar 150.

This forward movement causes the cam members 152a, 152b to travel along the inclined path of the cam surface 162a, 162b. As the first spring 120 expands its axial force is transmitted by the collar 150 through the fully compressed second compression spring 122 to the forward end of the plunger 110. However, initially the plunger 110 is unable to travel beyond the collar 150 as the radial projections 116 engage the internal flange 154 at the rear of the collar 150.

Due to the splined engagement between the trigger button 40 and the plunger 110 the collar 150 must rotate relative to the plunger 110, in the direction of the arrow B, as the cam members 152a, 152b travel along the cam surfaces 162a, 162b. The thrust washers 121, 122 prevent or reduce any frictional resistance to the rotation of the collar 150 by the springs 121, 122. As best seen in the end view of FIG. 4C, the resulting relative rotation of the collar 150 causes the aperture 155 to rotate relative to the radial projections 116a, 116b moving the projections off the stop surface 157 and towards the radial slots 156a, 156b.

Figure 5:
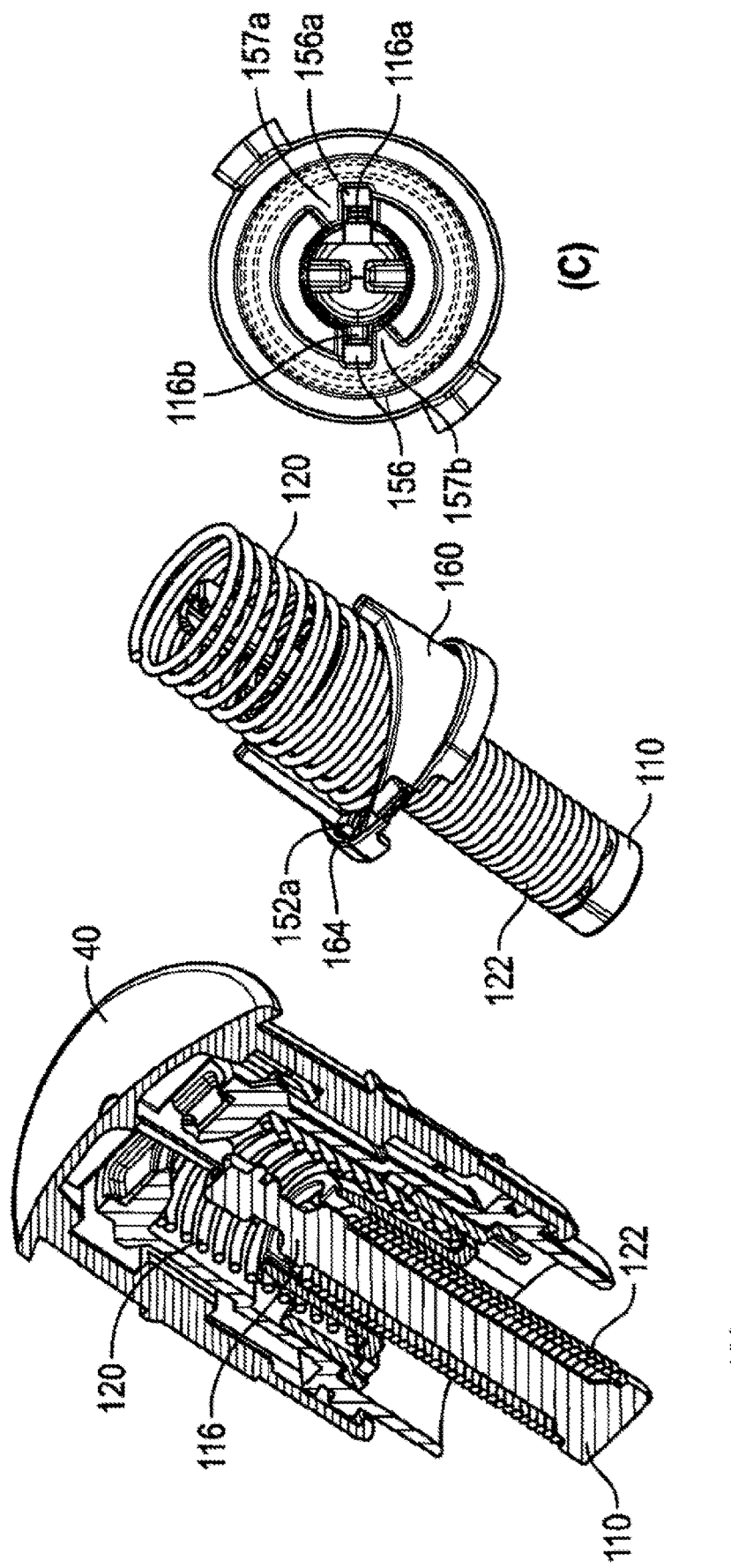

As the plunger 110 and collar 150 continue to move forwardly, the collar 150 reaches its fully rotated position as shown in FIG. 5. In the illustrated example the fully rotated position corresponds to approximately one half turn of the collar 150 (although the skilled person will appreciate that the particular configuration may vary depending on the profile of the cam surface and the required sequencing of the actuation mechanism 100). In this position the radial slots 156a, 156b have rotated into alignment with the radial projections 116a, 116b and the cam members 152a, 152b have also reached the end of the cam surface 162a, 162b and have moved into alignment with the cut-out/aperture 164 at the end of the cam path.

Figure 6:
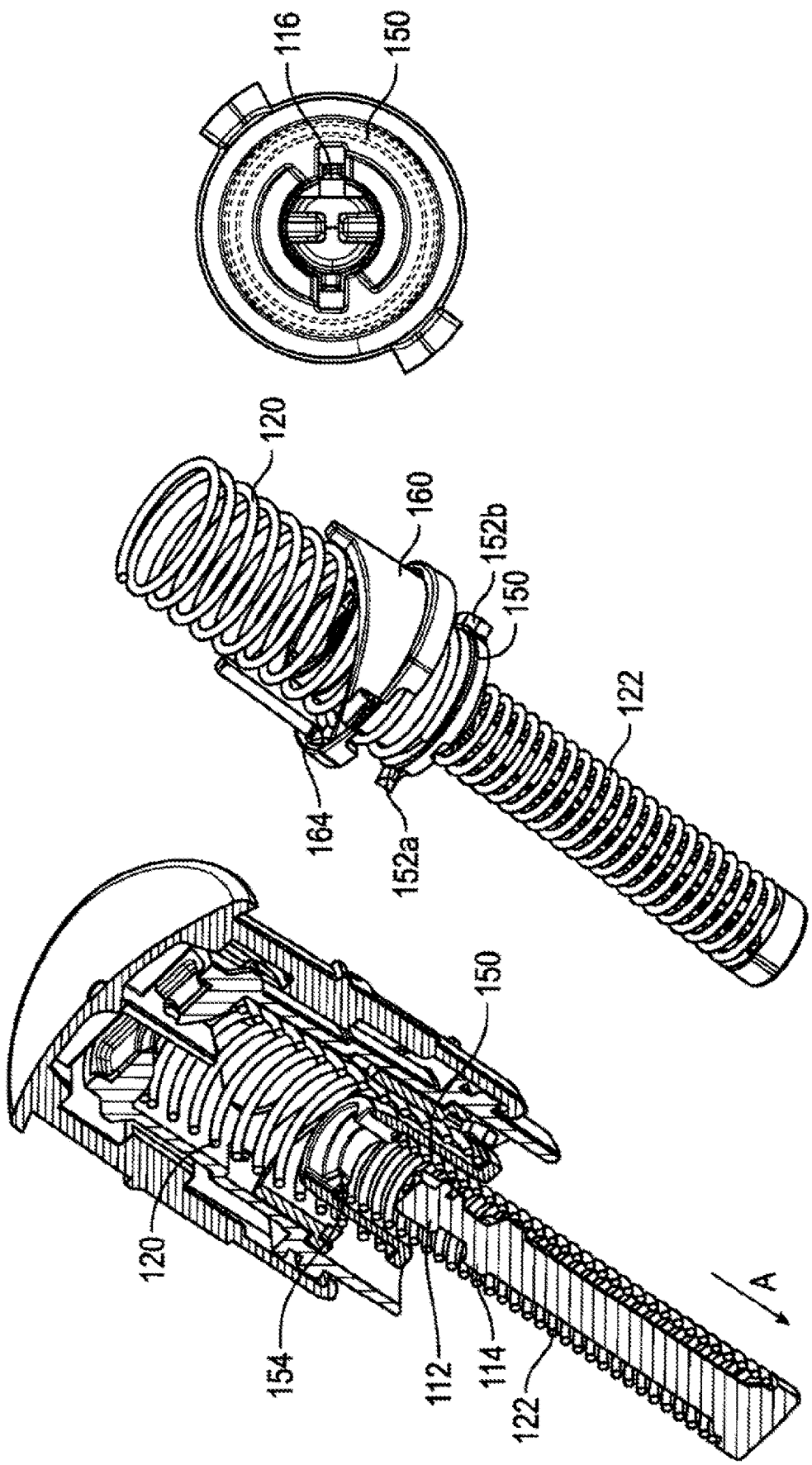

Accordingly, as shown in FIG. 6, the velocity regulator may now disengage so as to allow the plunger to continue freely forward (continuing in the direction of arrow A). In this forward movement the plunger 110 moves forward relative to the collar 150 due to the radial projections 116a, 116b passing through the radial slots 156a, 156b and the collar 150 is also allowed to pass forwardly of the cam body 160 due to the cam members 152a, 152b passing through the cut-outs 164. In other words, both the collar 150 and plunger 110 are disengaged and the collar 150 and cam body 160 are disengaged. In the illustrated embodiment the disengagements both occur substantially simultaneously (although the skilled person will appreciate that this may depend on the particular sequencing required). Once the radial projections 116a, 116b have passed through the radial slots 156a, 156b, the second drive spring 122 is free to expand and push against the collar 150 and plunger 110. The collar 150 is also free from the velocity regulator, and the first drive spring 120 and second drive spring 122 act on the plunger.

Once the velocity regulator is disengaged, the forward motion of the plunger 110 is no longer regulated (but the skilled person will appreciate that the plunger may now be pressing against the medicament within the syringe 5 such that its motion is naturally damped). The forces exerted by the springs 120, 122 on the plunger and the collar are dependent on the relative strengths of the first spring 120 and second spring 122, as well as the damping force provided by the medicament through the plunger 110. The axial motion of the collar 150 once the collar 150 has passed through the velocity regulator is therefore application-dependent.

Although the device has been described above with reference to one embodiment, it will be appreciated that various changes or modifications may be made. For example, the skilled person will appreciate that the timing of the disengagement between the components of the velocity regulator may depend on the particular configuration of the device. For example, the velocity regulator may be intended to slow/control the movement of the plunger 110 only during an initial movement in which the plunger 110 is brought into contact with the bung 7 of the syringe 5 (since manufacturing tolerances will usually make it necessary for the forward end of the plunger 110 to be initially spaced from the rearward end of the bung 7) so as to reduce impact thereto. Alternatively, or additionally, the velocity regulator may be configured to control the speed of movement of the actuation mechanism until the needle insertion step of the actuation process has been completed. Whilst the illustrated example includes two opposing counter-surfaces the skilled person will appreciate that more or less features may be utilised.

In the illustrated device the cam surface defines a substantially constant helical cam path but the skilled person will appreciate that the surface may have other sloped profiles (for example, a variable angle of incline) depending upon the velocity profile required for the forward movement of the plunger 110. Whilst an arrangement having two compression springs is advantageous in providing a compact actuation mechanism the skilled person will appreciate that in some embodiments only a single compression may be utilised. For example, in a single spring arrangement, the cam members could be formed on a portion of the plunger and the plunger may be allowed to rotate relative to the housing.

An alternative injection device or autoinjector 200 will now be described. Whilst this device may incorporate features of the device of FIGS. 1 to 6, it does not necessarily do so. Nonetheless the explanation of the prior art device will be helpful to the skilled person in understanding the structure and operation of the alternative device. As will be described in more detail, the principle feature of the alternative device is the provision of a velocity regulator to regulate the velocity on the plunger at the start of the delivery phase. This velocity regulation allows the end of the plunger to close any gap which initially exists between itself and the bung within the syringe body at a controlled velocity, preventing damage that might otherwise be caused by the end of the plunger impacting on the bung with a high velocity. Thereafter the velocity regulator is decoupled from the plunger allowing the full force of the delivery spring to be applied to the plunger and hence the bung. N.B. This velocity regulator differs from the velocity regulator described above which regulates velocity during the insertion phase. The velocity regulator described below may be used in conjunction with the prior art velocity regulator although this need not be the case.

Figure 8C:
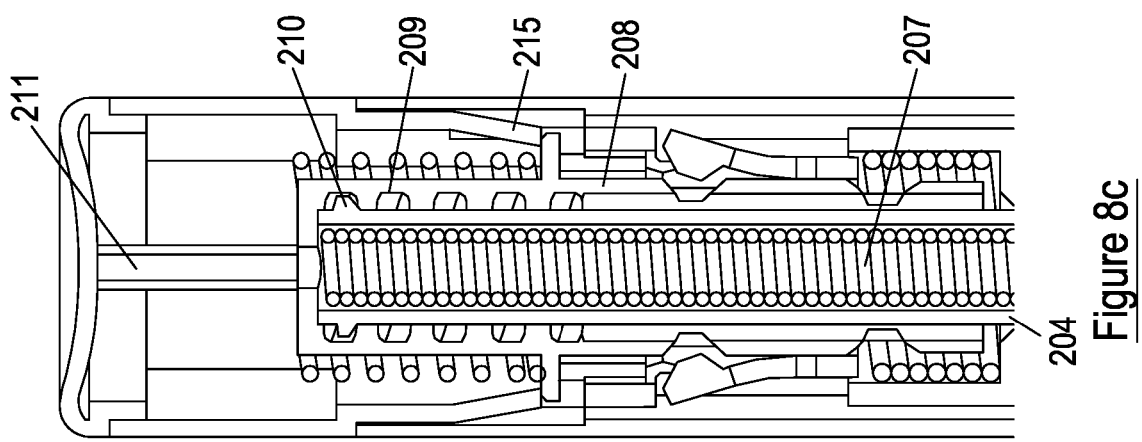
FIGS. 8A to 8C are sequential views corresponding to FIG. 7 during activation of an autoinjection device.
Figure 8B:
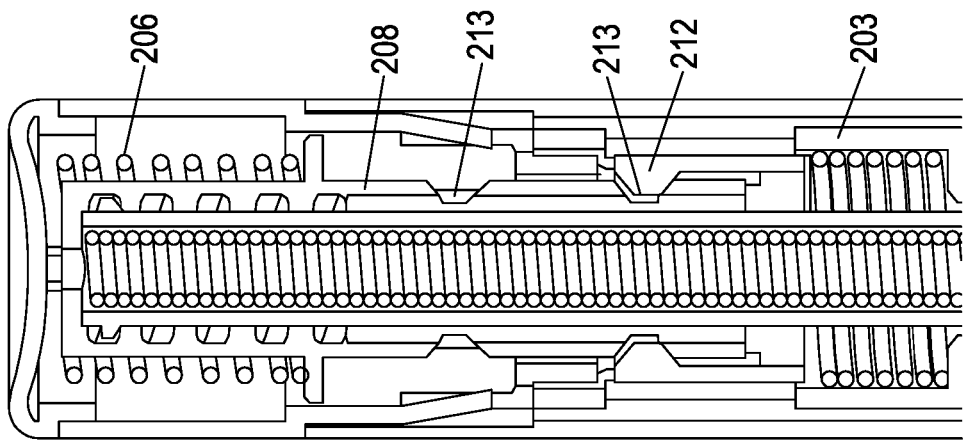
Figure 8A:
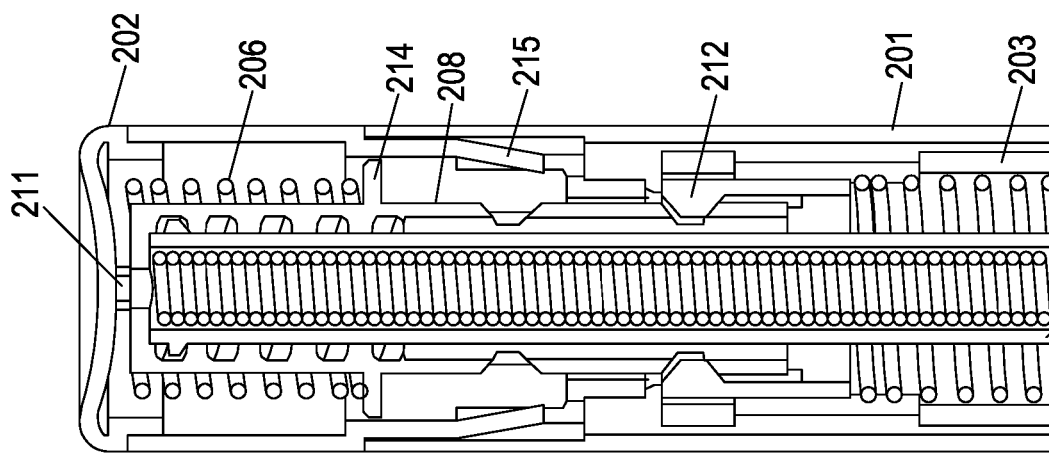

FIG. 7 illustrates an injection device 200 having this feature. Although not all features are described here, a number of components are pointed out in the Figure including a housing 201, cap 202, lock-out shroud 203, plunger 204, insertion spring 206, delivery spring 207, and sleeve 208. The device contains a syringe having a syringe body 300, a needle 301 and a bung 302 within the syringe body 300. FIG. 8 illustrates in more detail the upper part of the device in various operational configurations.

Considering further the construction of the upper part of the device, the plunger 204 has the general form of a hollow cylinder. An elongate pin 205 depends from the top of the sleeve 208, into the plunger 204, and is axially moveable with the sleeve 208. The delivery spring 207 is located inside the plunger 204 and surrounds the pin 205.

The insertion spring 206 acts at its upper end against the top end of the sleeve 208 such that it biases the sleeve 208 with respect to the cap 202. A screw thread 209 is provided inside the sleeve 208 at its upper end. A pair of projections 210 are provided on an outer surface of the plunger 204 and engage with the screw thread 209. The cap 202, which is fixed relative to the housing and cannot rotate, comprises a pair of opposing, depending legs 211. These legs 211 extend along axial slots provided in the sleeve such that the legs 211 intersect with the screw thread 209 to initially block rotation of the plunger 204 within the sleeve 208. The sleeve 208 cannot rotate within the housing but is able to move axially as will be described. The plunger 204 is biased forward by the delivery spring 207 against the sleeve 208. For the plunger 204 to travel axially it must rotate down the velocity regulator thread 209. The location of the cap legs 211 prevents this rotation and thus holds the plunger 204 in its stored state.

A collar 216 is located around the plunger and comprises at its upper end a number of sprung fingers 217 which are initially engaged with corresponding recesses in the outer surface of the plunger 204. The sprung fingers 217 are, during insertion, prevented from flexing outwards by features of the inside of the housing. During insertion the collar 216 therefore moves axially with the plunger 204. The bottom of the collar 216 is provided with a flange 218 which abuts the flange 304 of the syringe body 300.

In FIG. 7 the device is shown in four different operational configurations. The configuration on the left shows the device before use, with both the insertion spring 206 and delivery spring 207 compressed (also shown in FIG. 8A). In this configuration the syringe needle 301 is protected with a rubber boot 303. Immediately prior to performing an injection, the user removes the rubber boot 303. It will be seen from FIG. 8A that, in this state, a pair of legs 212 associated with the housing are engaged with respective detents 213 provided in an outer surface of the sleeve 208. These legs are prevented from moving outwards by the lock-out shroud 203 (or by some component fixed to the lock-out shroud). As such the insertion spring 206 is retained in a compressed state and the sleeve 208 is locked in place. The user can then press the end of the lock-out shroud 203 against the skin. Once the lock-out shroud 203 has been pushed sufficiently far into the device housing, the legs 212 are freed to flex outwardly, releasing the sleeve 208 from the housing. This configuration is shown in the second drawing of FIG. 7.

The insertion spring 206 is now able to expand, pushing the sleeve 208 and the plunger 204 (and the still compressed delivery spring 207) through the housing. As the collar 216 is still secured to the plunger 204 at this stage, the collar 216 pushes the syringe body 300 ahead of it, causing the needle 301 to penetrate the user's skin. This motion continues until the syringe bottoms out on stop features formed in the housing.

Bottoming out of the syringe occurs after stops 214 extending outwardly from the collar have snapped-in beneath a pair of flexible legs 215 associated with the housing. This is best seen in FIG. 8C. This prevents any rearward movement of the sleeve 208 within the housing.

At this stage, the features of the housing blocking the outward flexing of the sprung fingers 217 from the collar 216 are no longer engaged, allowing these fingers 217 to flex outwardly and release the collar 216 from the plunger 204. As will also be seen in FIG. 8C, the sleeve 208 has also moved relative to the cap 202 to an extent that the legs 211 are no longer engaged with the projections 210, releasing the plunger 204 to rotate within the sleeve 208 under the force exerted by the delivery spring 207. The plunger 204 begins to rotate down along the screw thread 209. As best seen in the third drawing in FIG. 7, the bottom of the plunger 204 moves down through the syringe body, closing any gap between the end of the plunger 204 and the bung 302, until the plunger 204 is in contact with the bung 302. This occurs whilst the velocity of the plunger 204 is controlled by the transition through the screw thread 209. The plunger 204 then starts to push the bung 302 though the syringe body 300 ejecting medicament through the tip of the needle 301. Shortly thereafter, the plunger 204 will have moved in an axial direction sufficient to disengage from the screw thread 209 in the sleeve 208. At this point the screw thread 209 ceases to inhibit the motion of the plunger 204, and the full force of the delivery spring 207 is freed to act on the bung 302.

It will be appreciated that various modifications may be made to the above described embodiment without departing from the scope of the invention. For example, rather than the plunger 204 rotating relative to the sleeve 208, the opposite may be the case. The locations of the screw thread 209 and the projections 210 may also be reversed.

The invention claimed is:

1. An injection device for delivering a medicament from a syringe contained, in use, within a housing of the device, the device being configured to move the syringe through the housing to cause insertion of a needle of the syringe into a user's skin and to subsequently move a bung of the syringe through a syringe body to deliver medicament through the needle, the device comprising:
   a plunger for engaging with said bung;
   a sleeve located around the plunger;
   an insertion spring biasing the sleeve relative to the housing;
   a delivery spring biasing the plunger relative to the sleeve;
   a release mechanism for releasing the sleeve from the housing to commence insertion and for releasing the plunger from the sleeve, following insertion, to commence delivery of the medicament, and
   a velocity regulator for regulating the velocity of the plunger upon its release from the sleeve and for disengaging from the plunger during delivery, the velocity regulator comprising a screw thread associated with one of the sleeve and the plunger and one or more thread engaging members formed on the other of the sleeve and the plunger, and
   wherein said release mechanism comprises features fixed relative to the housing and being in engagement with said screw thread prior to and during insertion, and being disengaged with the screw thread following insertion.

2. The injection device according to claim 1 and comprising a latching mechanism for latching the sleeve following insertion to prevent rearward movement of the sleeve.

3. The injection device according to claim 2, wherein said release mechanism comprises features provided on the sleeve for engaging directly or indirectly with features on a lock-out shroud of the device, engagement preventing axial movement of the sleeve within the housing and disengagement allowing the sleeve to move under the force exerted by the insertion spring.

4. The injection device according to claim 3, the velocity regulator being configured such that, after a predefined axial movement of the plunger said one or more thread engaging members is (are) disengaged from the screw thread allowing axial travel of the plunger.

5. The injection device according to claim 3, the velocity regulator being configured such that, after a predefined axial movement of the plunger said one or more thread engaging members is (are) disengaged from the screw thread allowing axial travel of the plunger.

6. The injection device according to claim 2, the velocity regulator being configured such that, after a predefined axial movement of the plunger said one or more thread engaging members is (are) disengaged from the screw thread allowing axial travel of the plunger.

7. The injection device according to claim 2, the velocity regulator being configured such that, after a predefined axial movement of the plunger said one or more thread engaging members is (are) disengaged from the screw thread allowing axial travel of the plunger.

8. The injection device according to claim 2 and comprising a collar located around the plunger, the collar being axially movable with the plunger during insertion in order to transfer force from the plunger or the sleeve to the syringe body, and being disengageable from the plunger following insertion in order to allow the plunger to move axially through the collar.

9. The injection device according to claim 1 wherein said release mechanism comprises features provided on the sleeve for engaging directly or indirectly with features on a lock-out shroud of the device, engagement preventing axial movement of the sleeve within the housing and disengagement allowing the sleeve to move under the force exerted by the insertion spring.

10. The injection device according to claim 9, the velocity regulator being configured such that, after a predefined axial movement of the plunger said one or more thread engaging members is (are) disengaged from the screw thread allowing axial travel of the plunger.

11. The injection device according to claim 9, the velocity regulator being configured such that, after a predefined axial movement of the plunger said one or more thread engaging members is (are) disengaged from the screw thread allowing axial travel of the plunger.

12. The injection device according to claim 9 and comprising a collar located around the plunger, the collar being axially movable with the plunger during insertion in order to transfer force from the plunger or the sleeve to the syringe body, and being disengageable from the plunger following insertion in order to allow the plunger to move axially through the collar.

13. The injection device according to claim 1, the velocity regulator being configured such that, after a predefined axial movement of the plunger said one or more thread engaging members is (are) disengaged from the screw thread allowing axial travel of the plunger.

14. The injection device according to claim 1 and comprising a collar located around the plunger, the collar being axially movable with the plunger during insertion in order to transfer force from the plunger or the sleeve to the syringe body, and being disengageable from the plunger following insertion in order to allow the plunger to move axially through the collar.

15. The injection device according to claim 1, the velocity regulator being configured such that, after a predefined axial movement of the plunger said one or more thread engaging members is (are) disengaged from the screw thread allowing axial travel of the plunger.

16. The injection device according to claim 1 and comprising a collar located around the plunger, the collar being axially movable with the plunger during insertion in order to transfer force from the plunger or the sleeve to the syringe body, and being disengageable from the plunger following insertion in order to allow the plunger to move axially through the collar.

* * * * *